(12) United States Patent
Foerster et al.

(10) Patent No.: US 8,715,297 B1
(45) Date of Patent: May 6, 2014

(54) FLAT SUTURE BANDING SYSTEM AND METHODS

(75) Inventors: Seth Arnold Foerster, San Clemente, CA (US); David Trottingwolf Aldridge, Laguna Hills, CA (US)

(73) Assignee: Dallen Medical, Inc., San Clemente, CA (US)

( * ) Notice: Subject to any disclaimer, the term of this patent is extended or adjusted under 35 U.S.C. 154(b) by 462 days.

(21) Appl. No.: 12/836,000

(22) Filed: Jul. 14, 2010

Related U.S. Application Data

(60) Provisional application No. 61/225,349, filed on Jul. 14, 2009.

(51) Int. Cl.
*A61B 17/10* (2006.01)

(52) U.S. Cl.
USPC .......................................................... 606/139

(58) Field of Classification Search
USPC .......................................... 606/139, 151, 157
See application file for complete search history.

(56) References Cited

U.S. PATENT DOCUMENTS

| | | | |
|---|---|---|---|
| 303,360 A | 8/1884 | Brunner | |
| 3,822,445 A | 7/1974 | Feng | |
| 4,279,248 A | 7/1981 | Gabbay | |
| 4,444,181 A | 4/1984 | Wevers et al. | |
| 4,535,772 A | 8/1985 | Sheehan | |
| 4,608,735 A * | 9/1986 | Kasai | 24/196 |
| 4,667,675 A | 5/1987 | Davis | |
| 4,730,615 A | 3/1988 | Sutherland et al. | |
| 4,813,416 A | 3/1989 | Pollak et al. | |
| 4,901,721 A | 2/1990 | Hakki | |
| 4,938,760 A | 7/1990 | Burton et al. | |
| 4,959,064 A | 9/1990 | Engelhardt | |
| 4,969,892 A | 11/1990 | Burton et al. | |
| 5,330,489 A | 7/1994 | Green et al. | |
| 5,339,870 A | 8/1994 | Green et al. | |
| 5,366,461 A * | 11/1994 | Blasnik | 606/151 |
| 5,571,105 A | 11/1996 | Gundolf | |
| 5,722,976 A | 3/1998 | Brown | |
| 5,797,915 A | 8/1998 | Pierson, III et al. | |
| 5,807,214 A | 9/1998 | Riazi | |
| 5,810,854 A | 9/1998 | Beach | |
| 5,849,012 A | 12/1998 | Abboudi | |
| 5,972,006 A | 10/1999 | Sciaino, Jr. | |
| 6,051,007 A | 4/2000 | Hogendijk et al. | |
| 6,066,160 A | 5/2000 | Colvin et al. | |
| 6,080,185 A | 6/2000 | Johnson et al. | |
| 6,471,715 B1 | 10/2002 | Weiss | |
| 6,540,769 B1 | 4/2003 | Miller, III | |
| 6,547,725 B1 | 4/2003 | Paolitto et al. | |
| 6,589,246 B1 | 7/2003 | Hack et al. | |
| 6,648,903 B1 | 11/2003 | Pierson, III | |
| 6,969,398 B2 | 11/2005 | Stevens et al. | |

(Continued)

*Primary Examiner* — Sameh Boles
(74) *Attorney, Agent, or Firm* — Stout, Uxa, Buyan & Mullins, LLP; Donald E. Stout (57) ABSTRACT

A surgical tensioning device for holding separated tissues in contact with one another. The device comprises a frame having two opposing first and second sides and a lower surface and an upper surface, and a band for extending through and around said separated tissues to be held together in conjunction with said frame. The band has two ends releasably attached to the sides of the frame. When the ends are secured to the sides of the frame, the band holds separated tissues together and establishes a path of tension along its length that extends linearly between the two ends of the band.

13 Claims, 7 Drawing Sheets

(56) References Cited

U.S. PATENT DOCUMENTS

| | | |
|---|---|---|
| 6,997,189 B2 | 2/2006 | Biggs et al. |
| 7,108,710 B2 | 9/2006 | Anderson |
| 7,341,558 B2 | 3/2008 | de la Torre et al. |
| 7,416,556 B2 | 8/2008 | Jackson |
| 7,722,632 B2 | 5/2010 | Rothstein et al. |
| 7,867,251 B2 | 1/2011 | Colleran et al. |
| 7,867,253 B2 | 1/2011 | McMichael et al. |
| 2002/0147449 A1 | 10/2002 | Yun |
| 2003/0093117 A1 | 5/2003 | Saadat |
| 2005/0075653 A1 | 4/2005 | Saadat et al. |
| 2005/0090827 A1 | 4/2005 | Gedebou |
| 2005/0149121 A1 | 7/2005 | Crombie et al. |
| 2005/0240203 A1 | 10/2005 | Fuseri et al. |
| 2005/0251209 A1 | 11/2005 | Saadat et al. |
| 2007/0073289 A1 | 3/2007 | Kwak et al. |
| 2007/0112385 A1 | 5/2007 | Conlon |
| 2007/0213725 A1 | 9/2007 | Hack |
| 2007/0276437 A1 | 11/2007 | Call et al. |
| 2007/0293863 A1 | 12/2007 | Reimels et al. |
| 2007/0293864 A1 | 12/2007 | Reimels et al. |
| 2008/0004624 A1 | 1/2008 | Olroyd |
| 2008/0015589 A1 | 1/2008 | Hack |
| 2009/0062853 A1 | 3/2009 | McMichael et al. |

\* cited by examiner

Prior Art

Fig. 3B

Prior Art

FLAT SUTURE BANDING SYSTEM AND METHODS

This application claims the benefit under 35 U.S.C. 119(e) of the filing date of Provisional U.S. Application Ser. No. 61/225,349, entitled Flat Suture Banding System, filed on Jul. 14, 2009, and expressly incorporated herein by reference, in its entirety. This application is also related to U.S. patent application Ser. No. 12/347,821, entitled Dynamic Suture Tensioning Device and filed on Dec. 31, 2008, U.S. patent application Ser. No. 12/406,902, entitled Knotless Dynamic Suture Tensioning Device and Methods and filed on Mar. 18, 2009, U.S. patent application Ser. No. 12/406,904, entitled Load Shaping for Dynamic Tensioning Mechanisms and Methods and filed on Mar. 18, 2009, U.S. patent application Ser. No. 12/406,909, entitled Dynamic Tissue Holding Device with Low Profile Spring and filed on Mar. 18, 2009, and U.S. patent application Ser. No. 12/815,989, entitled Suture Band Buckle and Methods and filed on Jun. 15, 2010. All of these related applications are commonly assigned and expressly incorporated herein by reference, in their entirety.

BACKGROUND OF THE INVENTION

The present invention is related to the general surgical repair of separated body tissues, and more particularly to internally fixating and stabilizing such body tissues, specifically bones.

In the present state of the art, there are a number of systems available to repair biological tissues separated in surgery or by injury. These products serve to approximate and stabilize the tissues so that healing may commence and provide compression in the interface to promote healing. Compression and stability are critical for proper anatomical healing of tissue. With the correct amount of compression applied to the interface of the tissue portions to be joined, signals are sent to the tissue, thus allowing the tissue to remodel in proper anatomical position. The amount of compression applied to the tissue interface needs to be appropriate to the type of tissue that is being healed.

Twisted wires are also typically used to keep bone fragments together so they may heal. Twisted wires only hold tension as long as the twisted wire pair remains stable. Often the wires untwist too soon, thus failing to keep the bone fragments together so that they may heal. Wires can also cut into the bone fragments, thereby allowing them to separate so that healing is difficult.

When it is necessary to access the thoracic cavity for a medical procedure, for example, it is required to cut the sternum into two pieces using a sternal saw. Once the procedure is completed within the thoracic cavity, the sternum must be repaired. For such repairs, it is known to use a dynamic compression device, such as the spring device A shown in FIG. 1. Some of the drawbacks of this typical device A, and others which are used include:

1. Bulky spring materials, while occupying substantial space, often do not store much energy. Some use polymer elastic bands, while other use coiled springs;

2. Wires are sometimes used to wrap the bones into position in compression with one another. However, wires can have sharp ends that can damage adjunctive tissues, and the wires can also cut into the bone, as mentioned above. Knot stacks in suture can interfere with the natural movement of surrounding tissues; and 3. Current banding systems that incorporate a biasing mechanism to achieve dynamic compression put the biasing mechanism in line with the band or suture. This practice competes with precious space at the healing site. Suture or bands are used to approximate tissues so that they may heal. It is desirable to obtain the best purchase possible on the tissue, so that the binding mechanics offered by the suture may be utilized. The best purchase is optimized by ensuring that the suture has the greatest contact area with the tissue. If a biasing mechanism is interfering with this concept, the biasing mechanism may diminish the suture's ability to hold the tissues together.

Bands are advantageous over wires for a number of reasons. A band, by definition, is wide. In being wide, a band distributes its forces over a wider surface area. This inhibits the band from digging into the bone, unlike wires. In being wide, a band affords a larger cross-sectional area whereby more material may be realized, thus presenting the opportunity to offer as much strength in the construct as is necessary to hold the bone fragments together. As such, bands address wires' two main weaknesses, namely, digging into the bone fragments being held together and, not having sufficient cross sectional area.

Bands have different attributes than wires, some of which are difficult to manage. With strength comes stiffness, as mentioned elsewhere herein. The larger cross-section of the band significantly increases the stiffness of the band. While stiffness and rigidity are good attributes in that they can stabilize the bone union, these attributes can also prevent the band from following the contours of the bone when inserted. This can lead to capturing tissues underneath the band that ultimately destabilize the union as the tissues continue to compress and disappear over time. Binding the band ends together can also impose some problems. Generally this involves a mechanism on one band end that interfaces with holes or slots or contours on the other band end. This creates a tensioning system that is incremental in nature. As in the twisted wire system, this mechanical interface of the two ends is the weakest link in the system. This mechanical interface becomes stronger as the incremental steps become larger. But larger incremental steps aren't conducive to fine tuning the tension, so this is problematic. Flat sutures have been used to tie tissues together but the residual tension supplied in such a knotted structure is insufficient for optimum healing. There is a lot of fuss/time associated with trying to keep and hold a desirable tension with these flat sutures. What is needed is an attachment means that provides variable tensioning. Another problem associated with all banding systems is that they tension by pulling asymmetrically to one side requiring constant re-centering while tensioning the band. What is needed therefore is a banding system with the ability to tension symmetrically without requiring re-centering of the band.

Buckles demonstrate many of the needed aspects of joining two strap ends together in surgery. However, what is needed is a buckle/strap system that has the ability to free one strap end from the buckle such that it can be attached to a needle, routed through tissue, simply detached from the needle, and then attached to the buckle.

SUMMARY OF THE INVENTION

The present invention pertains to a surgical tensioning device for holding separated tissues in contact with one another. Improved devices and techniques are disclosed for holding two tissue portions in a state of compression and tension that address and overcome these shortcomings in an innovative way.

The present invention comprises a frame or a buckle frame. The frame may be rigid and has two opposing first and second sides and a lower surface and/or lower side and an upper surface and/or upper side. The lower surface and/or lower side of the frame is the surface and/or side that is in contact with the tissue(s) being held together. In one embodiment, the two opposing first sides of the frame may be parallel to one another. The device further comprises a suture or band for extending through and/or around the separated tissues to be held together in conjunction with said frame. The suture or band has a first end, that is releasably securable to the first side of the frame and a second end that is releasably securable to the second side of the frame. Thus, when the first end of the band is secured to said first side after routing the first end through and/or around the tissues and the second end is secured to the second side of said frame, said suture or band holds the separated tissues in contact with one another and establishes a path of tension along its length that extends linearly between the two ends of the band.

In one embodiment, the band is sufficiently flexible to provide tension along its length. In another embodiment, the band or suture is substantially flat. Also, independently, in one embodiment, a needle may be secured to either the first or second end of the band or suture of the device. Preferably, the frame or buckle has an opening that is sized appropriately to allow the passage of a needle that is secured to an end of the band or suture. In addition, the surfaces of the frame, for example, the surfaces of the interior of the frame, are adapted to guide the band so that the band can be easily threaded into the frame or buckle. As discussed below, the surface of the bar and corresponding mating surface on the frame may be textured or roughened for holding the band more securely once tensioned.

In one aspect of the present invention, the first side of the frame of the present device comprises a member around which said first end of the band may be secured. The member may be in the form of a pin or bar and may be rigid. In addition, in a preferred embodiment, the first end of the suture or band may be directly attached to a needle and may be secured to the first side of said frame at the member on the first side with the aid of a knot after being routed through and around said tissues. The member in the first side of the frame may have a circular cross section or any other cross section. In addition, the member may be textured or roughened to provide improved performance, that is, to secure or knot the first end of the band better relative to when the surfaces are not textured, once the band is fully secured and tensioned.

In another aspect of the invention, the first side of the frame may further comprise a slot. In this embodiment, the device further comprises an attachment mechanism that is used to attach or secure the first end of the suture or band at the slot in the frame or buckle frame. The slot in the frame may be integral and is preferably sized and adapted to mate and lock with the attachment mechanism after the attachment mechanism has been routed through and/or around said tissues. In this embodiment, the attachment mechanism is preferably secured to first end of the band or suture on one end and a needle on the other end. The attachment mechanism may be secured to the first end of the suture or band via a loop. The attachment mechanism preferably comprises a tab that can pass through the slot in the frame. Once the attachment mechanism is inserted into the slot, the tab inserts into the slot and then pops out and engages into the slot, thus locking the attachment mechanism at the slot on the first side of the buckle frame. In addition, the attachment mechanism may comprise a tapered face and may be sufficiently rigid to promote cutting through the tissue, and furthermore, the tapered face of the attachment mechanism may be sharpened to promote cutting through the tissue. The attachment mechanism may further comprise notches designed to enable breaking of the attachment mechanism at such pre-defined location. Preferably such notches are used to easily remove or disengage the needle from the attachment mechanism.

In still another aspect of the invention, the present device further comprises a bar or pin that is moveably attached to the second side of the frame via an attachment. The bar or pin and bar attachment are adapted to hold tension across the suture or band by pinching the second band end between the bar and the second frame side. The bar attachment is adapted to mechanically constrain movement of the bar into the inside of the frame and away from the upper surface about the second side of frame. In addition, when the bar or pin has a circular cross section, the bar attachment is adapted to prevent rotational movement of the bar once it has been engaged to pinch the second band end between itself and the second frame side.

In yet another aspect of the invention, the bar is attached outside the second side of the frame via the bar attachment. In this embodiment, the bar attachment is adapted to mechanically constrain movement of the bar into the inside of the frame and away from the upper surface about the second side of frame. The bar can have any profile. In one embodiment, its profile is round, that is, it has a circular cross section. In the embodiment where the bar has a circular cross section, the bar attachment is adapted to prevent, in addition, rotational movement of the bar. Further, in this embodiment, the space between the first and second sides of the frame and the space between the bar and the outside of the second side may be substantially similar and sized to allow said band to pass through easily. Further, and independently, the surfaces of the bar and the outside of the second side of the frame, that is the mating surface for the bar, may be textured or roughened to provide improved performance, that is, to secure the second end of the band better relative to when the surfaces are not textured, once the band is tensioned.

In accordance with the device described above, when the second band end is routed around and through tissues being held together and from the bottom up through the center of the frame and over the second frame side and down between the second frame side and bar such that when second band end is tensioned and released, the bar holds the tension by pinching the band between the bar and second frame side.

In another embodiment, the bar is attached inside the frame at the second side of the frame via the bar attachment. In this embodiment, preferably, a support or buttress is provided inside the frame at the second frame side that includes an upper cam surface. The bar is attached at the second frame side, via a bar attachment, to the support on the upper cam surface of the support, so that the upper cam surface is contiguous with the upper surface of the frame at the second side of the frame. In this embodiment, the bar attachment is adapted to mechanically constrain movement of the bar into the inside of said frame and away from the upper surface of the frame and away from the support about the second side of frame. The bar can have any profile. In one embodiment, its profile is round, that is, it has a circular cross section. In the embodiment where the bar has a circular cross section, the bar attachment is adapted to prevent, in addition, rotational movement of the bar. The cam surface allows for supplying more leverage to the hinging attachment mechanism such that the bar can be forced harder into and be better locked inside the upper cam surface of the support against the second frame side. Further, in this embodiment, the space between the bar and the inside of the first side of the frame and the space between the bar and the inside of the second side are substantially similar and are sized to allow suture or band to pass through easily. Further and independently, the surfaces of the bar and the inside of the second side of the frame, that is the mating surface for the bar, may be textured or roughened to provide improved performance, that is, to secure the second end of the band better relative to then the surfaces are not textured, once the band is tensioned. In the embodiment of the device where a needle is attached to the second end of the band, the bar is adapted to move away from the second frame side to a sufficient distance so as to allow the needle to pass around the bar.

In accordance with the device described above, when the second band end is routed around and through tissues being held together and from the bottom up through the center of the frame and over the bar and down between the bar and second side of frame such that when second band end is tensioned and released, the bar holds said tension by pinching the band between the bar and second frame side.

In accordance with yet another embodiment of the present device is described a surgical tensioning device for holding separated tissues in contact with one another wherein the device comprises a frame with two opposing first and second sides, which are preferably parallel to each other, and a lower surface and/or lower side and an upper surface and/or upper side. The lower surface and/or lower side is the surface and/or side that is in contact with the tissue(s) being held together. The device further comprises a band or suture for extending around and/or through the separated tissues to be held together in conjunction with the frame. The band in this embodiment has a first end that is releasably securable to the first side of the frame and, a second end that is releasably securable to the second side of said frame. When the first and second ends are secured to both first and second sides of the frame, after either the first end or the second end or both ends are routed through and round the separated tissues to be held together, the band holds the separated tissues together and establishes a path of tension along its length.

In accordance with yet another embodiment of the invention is described a needle guide, adapted to be used in conjunction with any of the devices described above. The purpose of the needle guide is to mitigate or prevent any damage to the bars and attachments of the devices when a large needle of the kind used in these surgical repairs is used. The frame or buckle of the present devices has been designed to be small because this is a desirable quality for orthopedic implants. The needle used in these surgical repairs needs to be abnormally large so that it can pierce sternal bone. Sternal needles therefore are some of the largest needles made for threading sutures. The present needle guide removably fits or attaches to the frames of the present devices. The needle guide comprises slots, preferably integral slots so that the needle guide and slots are a single element, and is sized to fit via the slots over the bar in order to restrain the bar which, when placed over the bar, mitigates or prevents damage to the bar and bar attachment from the needle.

Once the frame of the present devices has been threaded with the suture and the bar(s) is set, the needle guide may be removed as it has no further function. This is desirable as this lowers the profile of the implant.

As used herein, the tissue portions to be held in contact with one another in the present invention comprise biological tissue in the body, including, but not limited to, skin, tendon, bone, ligaments, blood vessels, and organs. In one embodiment, the tissue portions comprise sternal bone that has been cut for a procedure to access the thoracic cavity.

The dermal layer on top of the sternum is rather thin. Even when a surgeon employs only twisted wire to repair the sternum, some patients can feel that wire under their skin. Consequently, the profile of a closure device can have cosmetic as well as practical concerns. The dermal layer over the sternum on an average adult female is 5 to 10 mm thick. A device that is ~5 mm in height is sufficiently thick to be rather clearly seen in some adults. The profiles of the current inventive devices are spread out over a large surface area, resulting in a much more favorable aspect ratio, it will not be easily seen when viewing the patient from the outside.

A particularly advantageous feature of the invention is that the aspect ratio of the inventive device, defined as the height of the device above the tissue surface, divided by the length of the device, is less than or equal to approximately 0.50, and more preferably approximately 0.10. In addition, the maximum height or profile of the current inventive device at the frame preferably is about 4 mm to about 1 mm.

In certain embodiments, the buckle or frame of the device is fabricated from either tempered stainless steel, spring tempered stainless steel or titanium.

In certain embodiments of the present invention, the pins or bars of the device are fabricated from either tempered stainless steel, spring tempered stainless steel or titanium.

In certain embodiments of the present invention, attachments or straps of the device are fabricated from either spring tempered stainless steel or titanium.

In one embodiment, the band or suture of the present devices is sufficiently flexible to provide tension along its length. In yet another embodiment, the band or suture is substantially flat. The suture or band may be defined by that which is normally available. It may be woven fibers or a monofilament and can be any material. Accordingly, the band may comprise woven, braided, or knitted fibers or metals, or a monofilament, and can be made of any known suture material. The suture may be of any shape, including, but not limited to, round, square, oval, flat (like a strap), or tubular. The shape of the suture or band for particular embodiments will be discussed more fully herein below. In one embodiment of the inventive device, the suture preferably comprises flat or tape suture.

On one end of the suture or band may be a needle or other receptacle to facilitate stitching or weaving in tissue or bone. Accordingly, in one embodiment, a needle may be secured to the second end of the band or suture of the device. Alternately, a needle may be secured to both ends of the suture.

In another aspect of the invention, there is described an advantageous method of repairing separated tissues using a tissue tensioning device comprising a frame having opposing first and second sides, a lower surface, and an upper surface, and a band having a first end and a second end. The method comprises steps of routing a needle attached to the second end of the band through the separated tissues and into close proximity to the second side of the frame, separating the needle from the second end of the band, and securing the second end of the band to the second side of the frame. In one embodiment of the invention, the separating step is performed by cutting the needle away from the second end of the band. The securing step is performed by simply wrapping the second end of the band around the second side of the frame and tying a knot in the band.

In another approach, the separating step is performed by applying tension to the band at a point of weakness in order to break the band. A disclosed point of weakness comprises one or more notches formed in the band. Other known techniques, such as perforation, for creating such points of weakness may be used as well. The securing step comprises inserting an attachment mechanism on the second end of the band into a slot in the second side of the frame. The attachment mechanism comprises a tab which moves to an expanded position after the tab passes through the slot, in order to secure the attachment mechanism to the second side of the frame.

The invention, together with additional features and advantages thereof, may best be understood by reference to the following description taken in conjunction with the accompanying illustrative drawings.

DESCRIPTION OF THE PREFERRED EMBODIMENTS

Figure 1:
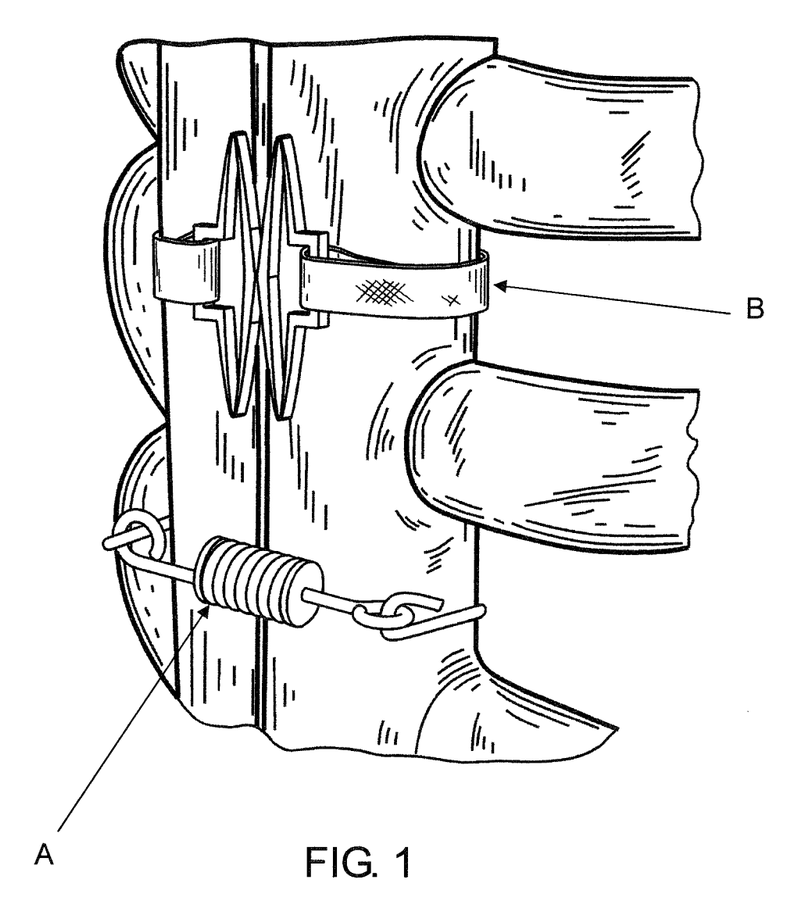
FIG. 1 is a view showing a sternum and illustrating how wires and bands might be used in binding sternal halves together for healing after open heart surgery.

Referring now more particularly to the drawings, there is shown in FIG. 1 an example of how wires and bands might be used in binding sternal halves together for healing after open heart surgery. As noted above, two different devices are shown side by side, for comparative purposes. Device A is a prior art spring device, while Device B is an inventive device described in related application Ser. No. 12/406,909.

Figure 2A:
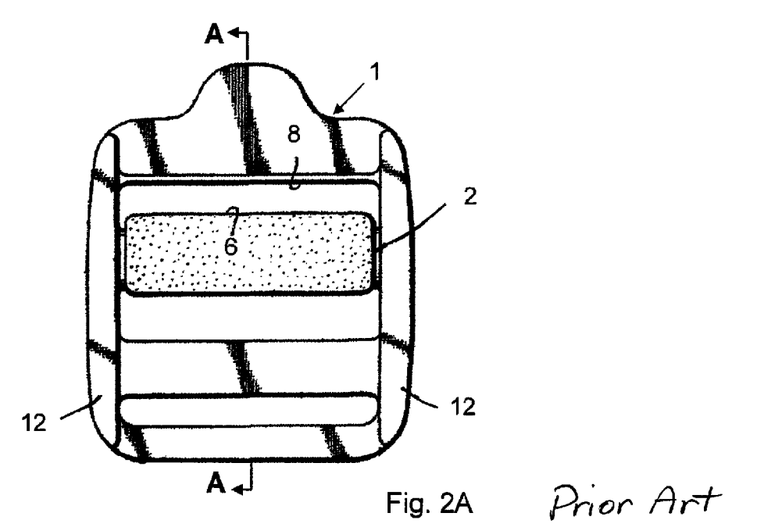
FIG. 2A is a top view of a common buckle.
Figure 2B:
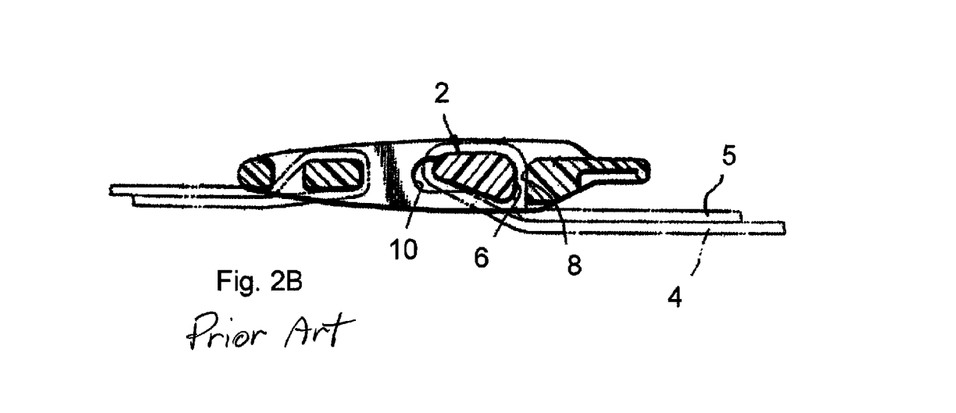
FIG. 2B is a cross sectional view of the buckle in FIG. 2A used with a strap.

A strap locking system similar to that shown in FIG. 1, with a common buckle 1 is represented in FIGS. 2A and 2B. A common buckle 1, of a type sometimes used for straps on bags, is suitable for use in this application because of its variable tensioning abilities. Lock bar 2 moves surface 6 away from surface 8 when strap tail 5 is tensioned. As strap tail 5 is tensioned, strap tail 4 is pulled into the 6/8 surface interface. When strap tail 5 is released, strap tail 4 holds the dominate tension which pulls lock bar 2 so that the strap is pinched between surfaces 6 and 8. This is the locked position of the buckle 1. Locking bar 2 is held in position by tabs on both of its ends. The tabs ride in a slot 10 which is cut out of frame 12. Slot 10 is critical in the operation because it holds face 6 on locking bar 2 so that it correctly pinches the strap against surface 8. The variability of the tension in each of strap tails 4 and 5 cause the lock bar to move in slot 10. The lock bar naturally wants to even out these tensions by rotating in slot 10. Flats are milled in the lock bar 2 ends to ride in slot 10 so that such rotation does not happen.

This buckle 1 generally has the means to provide variable tensioning to the strap loop. However with a suturing system, it is necessary to have one of these strap ends free so that it may be routed through tissue with a common suture-end-needle arrangement.

Of course, a common buckle 1, such as that illustrated, comes pre-threaded. What is needed to make a buckle suitable for a suture application is to have the buckle designed so that it might be threaded by the surgeon. In its common configuration, there is not enough room around locking bar 2 to fit a suture needle.

The distance the locking bar 2 has to travel to achieve the aforementioned locking and unlocking functionality is rather small. Therefore, the slots 10 provided for accommodating the locking bar ends are not long. Should the system be scaled down to the size of a 5 mm wide suture band, the slot 10 only needs to be 0.020 inches long. At this size, however, the slot does not provide bar travel sufficient to allow a common needle, 0.065 inches in diameter, to be threaded through the buckle. Furthermore, it would be difficult to make this common buckle design open up enough to make such threading easy. Surgeons would like to see an obvious opening for the needle to pass through.

Figure 3A:
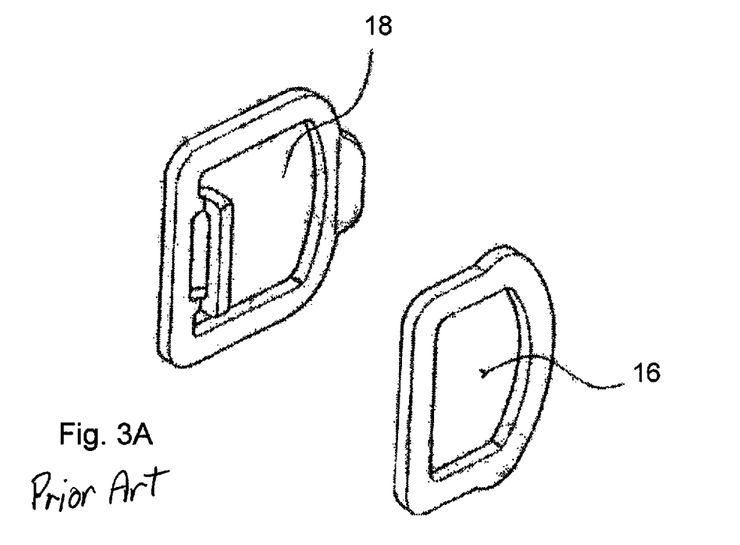
FIG. 3A is a perspective view of plates used in a common buckle.
Figure 3B:
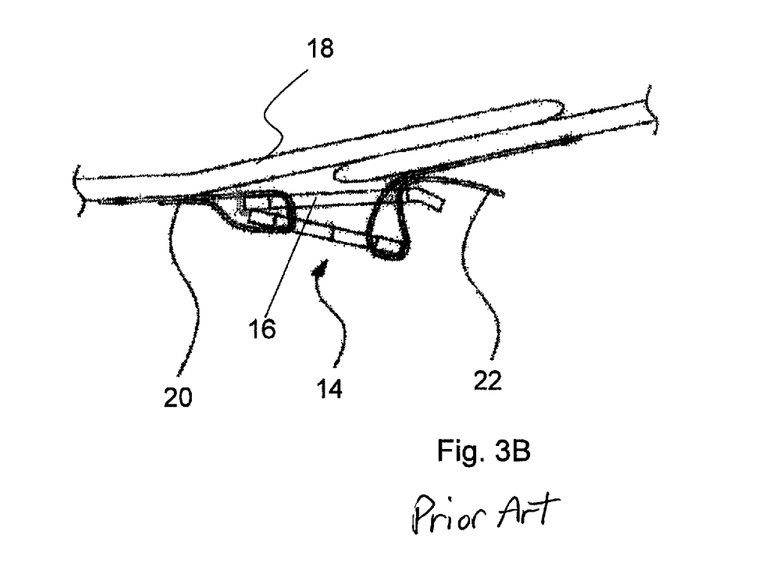
FIG. 3B is a cross sectional view of the buckle in FIG. 3A used with a strap.

A strap locking system similar to common buckle 2 is represented in FIGS. 3A and 3B. This system 14 shown in FIGS. 3A and 3B comprises two plates 16 and 18 that are joined by strap loop 20 (shown in FIG. 3B) at one end. Plate 16 is made smaller than plate 18 so that strap end 22 is pinched between adjoining surfaces on plates 16 and 18 when threaded as shown in FIG. 3B and then tensioned. The locking difference between plate system 14 and common buckle 1 lays in the pinching mechanism. Plate system 14 moves plate 16 on a hinge to lock and release strap 22. Plate 16 can only lay parallel to plate 18 and thus the surfaces on the locking mechanism are confined to plate surfaces as managed by the hinging action. These constraints limit the effectiveness of the locking abilities of plate system 14. The pinching surfaces are commonly only lines. Common buckle 1 can have any approach to the pinching system as defined by slot 10 and pinching surfaces 6 and 8 can be of any shape. Strap locking system 14 is interesting because it can be easily threaded by a suture-needle construct.

Figure 4:
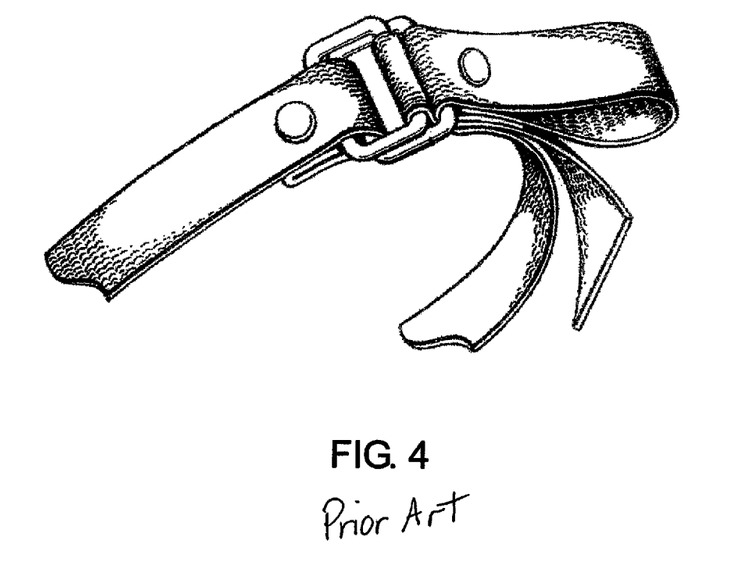
FIG. 4 is a perspective view of a buckle design where wires are used instead of plates.

FIG. 4 shows a similar buckle design as in FIG. 3 where wires are used instead of plates. The pinching surfaces are only opposing lines on either wire. As with the plate system 14, this wire buckle system may be threaded with the loose strap end. This works fine as long as the buckle is big enough to be manipulated with fingers. But when the buckle gets small on the scale of a 5 mm tape suture, the buckle becomes too small to manipulate for threading.

The present invention is directed to a strap buckle system that is prethreaded, has good strength holding characteristics, and is small so as to be used with suture sized straps. Furthermore, the present invention provides for holding the buckle open so that it may be easily threaded by a needle/suture construct.

The tissue portions to be held in contact with one another in the present invention comprise biological tissue in the body, including, but not limited to, skin, tendon, bone, ligaments, blood vessels, and organs. In one embodiment, the tissue portions comprise sternal bone that has been cut for a procedure to access the thoracic cavity. The suture may comprise woven, braided, or knitted fibers or metals, or a monofilament, and can be made of any known suture material. The suture may be of any shape, including, but not limited to, round, square, oval, flat (like a strap), or tubular. The shape of the suture for particular embodiments will be discussed more fully hereinbelow. In one embodiment of the inventive device, the suture preferably comprises flat or tape suture.

In certain preferred embodiments, the buckle or frame of the device is fabricated from either tempered stainless steel, spring tempered stainless steel or titanium.

Figures 5A, 5B:
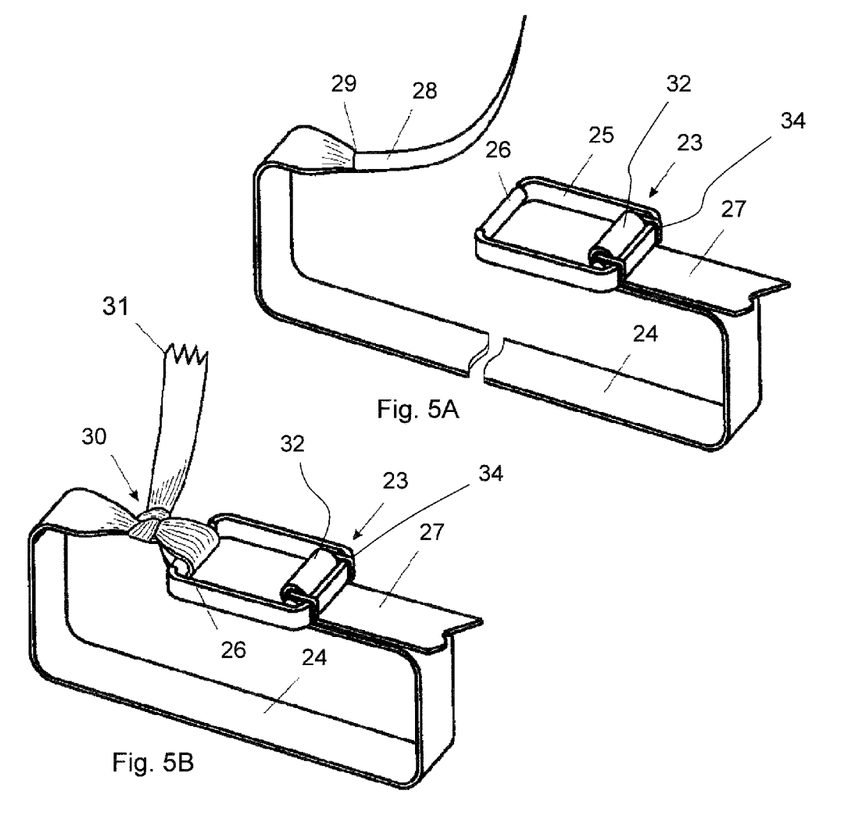
FIG. 5A is a perspective view of a portion of a banding suture system in accordance with an embodiment of the present invention wherein one end of the suture is pre-threaded into a buckle and the other end is attached to a needle.
FIG. 5B is a perspective view of the banding suture system shown in FIG. 5A wherein both ends of the suture have been secured.
Figure 5C:
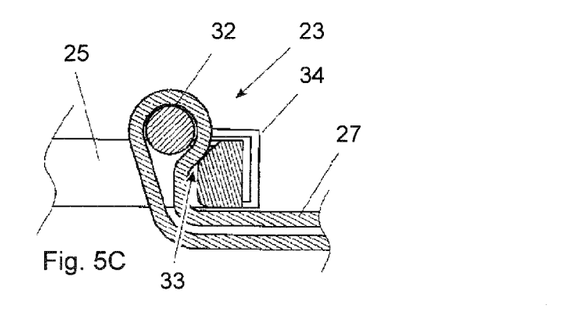
FIG. 5C is a cross sectional view of the buckle into which the second loose end of suture has been secured at the buckle.

FIG. 5 represents one embodiment of the invention. As shown in FIGS. 5A, 5B and 5C, a rigid frame 25 contains a member 26 on one end or side and buckle 23 on the other end or opposing side end with a member 32 linked via attachments 34 to frame 25 at this opposing end or side. The member 26 is preferably in the form of a substantially rigid pin or bar in this embodiment. The member 32 is preferably in the form of a substantially rigid pin or bar in this embodiment. Attachments 34 are preferably in the form of straps in this embodiment. These attachment members that link the rigid pin or bar 32 to the frame 25, are preferably constructed to yield to slight pressure and form around frame 25. Pin or bar 32 ultimately pinches the suture, band, or strap up against the inside surface of frame 25 at 33. Suture or band or strap 24 has a first end or tail 31 that is attached to needle 28 at a junction 29, and is attached to the frame 25 around bar or pin 26 as described herein. Suture or band 24 is pre-threaded through the buckle 23 so that the other tail or second end 27 of the suture or band is easily threaded into buckle 23 through a window (not shown) held open by attachment straps 34. As tension is applied to suture tail 27, the pin or bar 32 rotates to move from the outside of frame 25 to the inside of frame 25. Attachment straps 34 yield and form around frame 25 in this process. The straps serve to hold the pin in proper position to pinch the suture against the inside surface of frame 25 when tension is released on suture tail 27. Straps 34 also keep the bar or pin 32 from rotating.

During surgery, the above embodiment is used as follows. Needle 28 is routed through or around tissue and then into frame 25 and around pin 26. A knot 30 is then tied in the suture end around pin 26. Needle 28 can be removed before or after this step by simply cutting the suture/strap 24 at suture end 31 with scissors. Buckle 23 is then activated to approximate tissues by pulling on suture end 27. Locking pin 32 works in concert with straps 34 to loosen the buckle, thereby allowing the suture to pass through the buckle. When suture end 27 is released, suture gets pinched at 33 in the buckle 23.

In the above embodiment, the second end 27 of the suture/strap 24 comes pre-threaded in the buckle. The other or first end 31 comes attached to needle 28 for passing suture end through tissue. First suture end 31 is then tied in a knot that attaches it to the buckle. The needle is easily removable from the suture end. The buckle/suture construct or flat suture band system is now complete in a few easy steps, realizing the goals of the present invention.

Although round bars or pins are shown as engaging against flat surfaces in this embodiment, contoured pins with contoured mating surfaces on the pin and frame respectively, may be used to increase the buckle's holding performance. The mating surfaces, contoured or otherwise, may be further roughened or textured if more performance or better grip or holding is required.

In certain preferred embodiments of the present invention, the pins or bars of the device are fabricated from either tempered stainless steel, spring tempered stainless steel or titanium.

In certain preferred embodiments of the present invention, attachments or straps of the device are fabricated from either spring tempered stainless steel or titanium.

Buckle 23 has attachment straps 34 that perform the same function as slot 10 does in the buckle 1, yet the buckle 23 is simple enough to allow the free second end of suture 27 to be threaded through the buckle. Attachment straps 34 provide the same two functions slot 10 does in buckle 1; first to guide the pin into its mating locking inside frame 25, and second to keep the pin or bar 32 from rotating in the lock. Attachment straps 34 also hold a window open to allow the threading of free suture end 27. Although the buckles represented in FIGS. 3 and 4 are capable of being threaded, it would be difficult to manage with gloved fingers on such a small scale. This is all done in a low profile device as is required for such surgical implants. A downsized version of buckle 1 would have a larger profile due to the material needed around the slots.

Figure 6A:
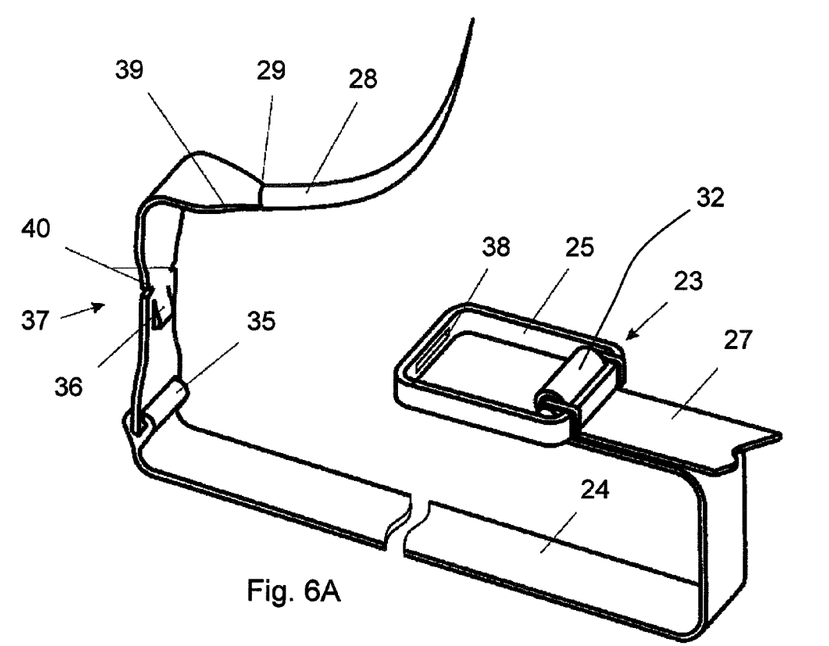
FIG. 6A is a perspective view of a portion of a banding suture system in accordance with an embodiment of the present invention wherein one end of the suture is pre-threaded into a buckle and the other end is attached to a needle.
Figure 6B:
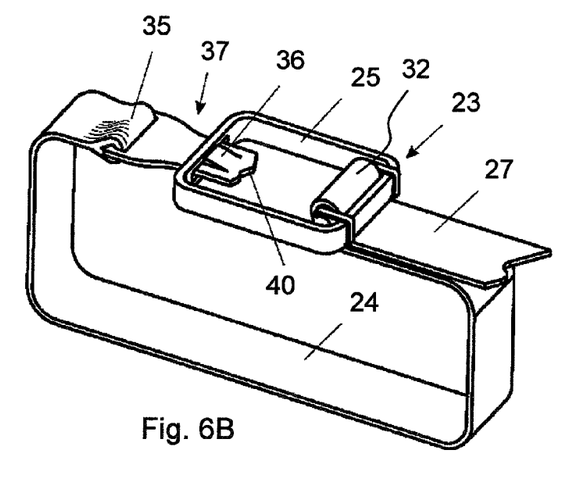
FIG. 6B is a perspective view of the banding suture system shown in FIG. 6A with the suture at the both ends secured.

FIGS. 6A and 6B show another advantageous embodiment of the invention. In this embodiment, the knots 30 of the prior embodiment, shown in FIG. 5B, are replaced with a different attachment mechanism. The buckle 23 is otherwise as shown in the prior embodiment. In this embodiment, the suture or strap 24 is attached to a member or bar on the attachment mechanism 37 by means of a loop 35. The frame 25, in the place of the member 26 on the first side of the frame in the embodiment of FIGS. 5A-5C, has a slot 38 that is sized and adapted to mate and lock with a member 36 in attachment mechanism 37. Attachment mechanism 37 is adapted to follow needle 28 that is attached to attachment mechanism 37 at junction 29 through the tissue and then become attached to buckle frame 25. Attachment mechanism 37 comprises a tapered face 39 that ends in junction 29 at which needle 28 is attached. Attachment mechanism 37 may be made of any material that is rigid enough to enable cutting tissues. Such material may comprise tempered stainless steel or titanium, for example, in currently preferred embodiments. In addition, the tapered face 39 might be further sharpened to promote tissue cutting. The attachment mechanism preferably has notches 40, or other suitable weakening mechanisms, such as perforations, designed to enable breaking of the suture or strap 24 at a predefined location. This enables easy removal of the needle 28, without the need for a cutting implement, such as scissors, and exposes tab 36 so that it may engage with slot 38.

This embodiment of the invention may be used as follows. Needle 28 is routed through separated tissues and in doing so, needle 28 brings attachment mechanism 37 and the attached suture or strap 24 though these tissues. Needle 28 is brought into close proximity to buckle frame 25. Attachment mechanism 37 is then broken along notches 40. Attachment mechanism 37 is then inserted into slot 38 in buckle frame 25. Attachment mechanism is then inserted until tab 36 pops through slot 38 and expands, as shown, thus locking the attachment mechanism 37 to buckle frame 25. Suture or strap tail 27 is then pulled to bring the tissues together.

In the above embodiment, the second end 27 of the suture/strap 24 comes pre-threaded in the buckle. The other or first end 31 comes attached to needle 28 via an attachment mechanism 37 for passing the suture end through tissue. First suture end 31 is then attached to the buckle frame via the attachment mechanism 37 after the easy removal of needle 28 using the notches 40 in the attachment mechanism 37. The buckle/ suture construct or flat suture band system is now complete in a few easy steps, realizing the goals of the present invention.

Figure 7A:
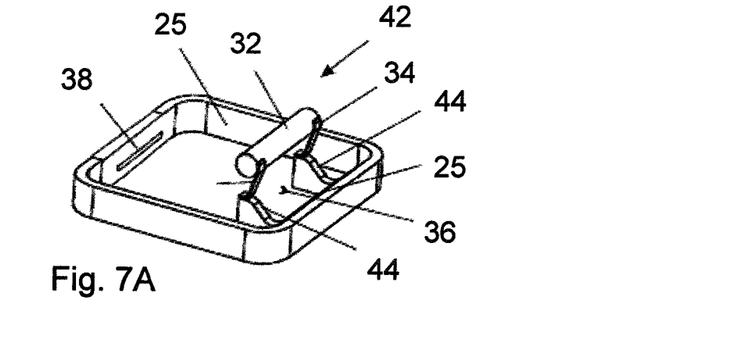
FIG. 7A is a perspective view of a portion of a band suture frame in accordance with an embodiment of the present invention without the suture band.
Figure 7B:
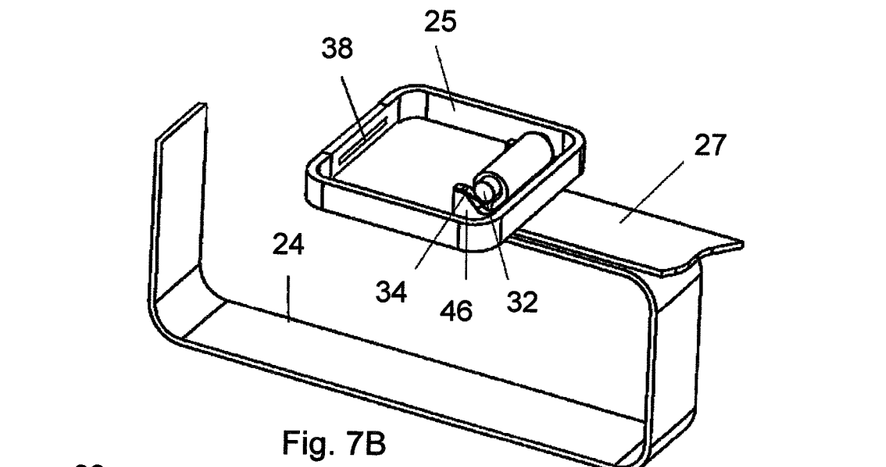
FIG. 7B is a perspective view of the banding suture frame shown in FIG. 7A including the suture with one end of the suture secured into the buckle.
Figure 7C:
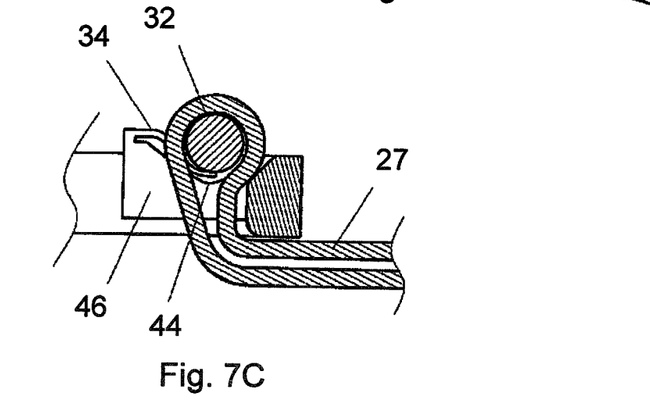
FIG. 7C is a cross sectional view of the buckle into which one end of suture has been secured.

FIGS. 7A-7C illustrate still another embodiment of the present invention, with a buckle 42 which is similar to the embodiment in FIGS. 6A and 6B in that it has a similar frame 25 with a slot 38, and a bar or pin 32, as well as attachment straps 34. Alternatively, in another embodiment (not shown), the frame could be similar to the frame 25 with a member 26 on the first side, as shown in FIGS. 5A-5C. Accordingly, the suture band may be secured at the first end 31 using an attachment mechanism 37 as shown in FIGS. 6A-6B, wherein the tab 36 locks into slot 38, or, a knot may be tied at the suture end 31 as shown in FIGS. 5A-5C when the frame has a member 26.

In the embodiment depicted in FIGS. 7A-7C, straps 34 start in the interior of the frame instead of outside the frame. This is managed by placing a buttress 42 on the interior of the frame and supplying a cam surface 44 to aid the straps in guiding the bar or pin 32. Consequently space 36 is supplied inside the frame for threading loose suture end 27. All the same advantages are realized with buckle 42 as with buckle 23. Buckle 42 has the additional advantage of having a simple threading route whereas the threading route through buckle 23 is a bit more complicated.

The cam surface 44 and strap 34 combination provide the same two functions as does slot 10 in FIG. 2; first to guide the pin into its mating locking inside surface of frame 25, and second to keep pin 32 from rotating in the lock. Cam surface 44 has the additional advantage of supplying more leverage to the hinging strap mechanism such that pin 32 is forced harder into and better locked inside surface. Although round bars or pins are shown in this embodiment, contoured pins with contoured mating surfaces on the pin and frame respectively, may be used to increase the buckle's holding performance. The mating surfaces, contoured or otherwise, may be further roughened or textured if more performance or better grip or holding is required.

While the inventive concept is disclosed as being particularly adapted for use in repairing the sternum after a thoracic cavity procedure, it is, of course, applicable to a great many other procedures requiring repair of bodily tissue, particularly bone.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. A surgical tensioning device for holding separated tissues in contact with one another, the device comprising:
   a frame, said frame having two opposing first and second sides, said first side comprising a rigid first member, a lower surface, and an upper surface;
   a band for extending through and around said separated tissues to be held together in conjunction with said frame, said band having a first end that is releasably securable to the first side of said frame at said first member, and a second end that is releasably securable to the second side of said frame, wherein, when the first end is secured to said first side after routing the first end through and around said tissues and the second end is secured to said second side of said frame, said band holds said separated tissues together and establishes a path of tension along its length that extends linearly between the two ends of the band; and
   a bar moveably attached parallel to the second side of said frame via a bar attachment, said bar and attachment being adapted to hold said tension by pinching said second band end between said bar and second frame side;
   wherein said bar is attached inside the frame at the second side via said bar attachment, the bar attachment being configured to mechanically constrain movement of said bar into the inside of said frame and away from said upper surface about the second side of frame and comprising a cam surface disposed within said frame for guiding said bar into a mating locking position against the inside surface of said second frame side to pinch said second band end between said bar and second frame side.

2. The device of claim 1, wherein said first side of said frame comprises a rigid member to which said first end of the band is secured.

3. The device of claim 1, wherein said first end of said band is directly attached to a needle.

4. The device of claim 1 wherein said bar has a circular cross section and said bar attachment is adapted to constrain said bar from rotational movement.

5. The device of claim 1 wherein said band is substantially flat.

6. The device of claim 5, where said band comprises suture.

7. The device of claim 1 wherein the surfaces of said bar and the inside of said second side of said frame are textured.

8. The device of claim 1, wherein said first side of said frame further comprises an integral slot that is sized and adapted to mate and lock with an attachment mechanism which is disposed on the first end of the band.

9. The device of claim 8, wherein said attachment mechanism further comprises a tab for mating with said slot.

10. A surgical tensioning device for holding separated tissues in contact with one another, the device comprising: a frame having opposing first and second sides, a lower surface, and an upper surface; a band for extending through and around the separated tissues to be held together, in conjunction with said frame, said band having a first end that is releasably securable to the first side of said frame and a second end that is releasably securable to the second side of said frame, said band first end being directly attached to a needle, wherein, when the first end is secured to said first side after routing the first end through and around said tissues and the second end is secured to said second side of said frame, said band holds the previously separated tissues in contact with one another and establishes a path of tension along its length that extends linearly between the two ends of the band; a bar moveably attached parallel to the second side of said frame via a bar attachment, said bar and attachment being adapted to hold said tension by pinching said second band end between said bar and second frame side, wherein said bar is attached inside the frame at the second side via said bar attachment, the bar attachment being configured to mechanically constrain movement of said bar into the inside of said frame and away from said upper surface about the second side of frame and comprising a cam surface disposed within said frame for guiding said bar into a mating locking position against the inside surface of said second frame side to pinch said second band end between said bar and second frame side.

11. The device of claim 10, and further comprising weakening mechanisms in the first end of the band for facilitating separation of the needle from the second end of the band.

12. The device of claim 11, wherein said weakening mechanisms comprise notches.

13. The device as recited in claim 10, wherein said first side of said frame further comprises an integral slot that is sized and adapted to mate and lock with an attachment mechanism which is disposed on the first end of the band.

* * * * *